(12) United States Patent
Spichiger-Keller et al.

(10) Patent No.: US 8,114,509 B2
(45) Date of Patent: Feb. 14, 2012

(54) METAL OXIDE MEMBRANE WITH A GAS-SELECTIVE COMPOUND

(75) Inventors: Ursula Spichiger-Keller, Au (CH); Stephan Spichiger, Au (CH); Jorge Fernando Fernandez-Sanchez, Atarfe (ES)

(73) Assignees: Eidgenossische Technische Hochschule Zurich (CH); Universidad De Granada (ES)

( * ) Notice: Subject to any disclaimer, the term of this patent is extended or adjusted under 35 U.S.C. 154(b) by 653 days.

(21) Appl. No.: 11/920,030

(22) PCT Filed: May 10, 2006

(86) PCT No.: PCT/EP2006/004396
§ 371 (c)(1),
(2), (4) Date: Jan. 26, 2009

(87) PCT Pub. No.: WO2006/119986
PCT Pub. Date: Nov. 16, 2006

(65) Prior Publication Data
US 2009/0199619 A1    Aug. 13, 2009

(30) Foreign Application Priority Data
May 10, 2005   (EP) ..................................... 0501063

(51) Int. Cl.
*B32B 3/26* (2006.01)
*G01N 33/00* (2006.01)
*B05D 5/06* (2006.01)

(52) U.S. Cl. ............... 428/312.2; 428/312.8; 428/315.5; 428/315.7; 428/316.6; 428/317.9; 428/319.1; 428/689; 428/702; 427/162; 427/419.1; 427/419.2; 73/23.2

(58) Field of Classification Search ......................... None
See application file for complete search history.

(56) References Cited

U.S. PATENT DOCUMENTS

| | | | |
|---|---|---|---|
| 5,342,431 A | 8/1994 | Anderson et al. | |
| 5,364,797 A | 11/1994 | Olson et al. | |
| 5,490,490 A | 2/1996 | Weber et al. | |
| 5,494,640 A | 2/1996 | Simon et al. | |
| 5,624,640 A | 4/1997 | Potthast et al. | |
| 5,858,457 A | 1/1999 | Brinker et al. | |
| 5,979,423 A | 11/1999 | Poindexter et al. | |
| 6,156,419 A | 12/2000 | Brugger et al. | |
| 6,251,342 B1 | 6/2001 | Narula et al. | |
| 6,704,470 B1 | 3/2004 | Schneider et al. | |
| 6,819,811 B1 | 11/2004 | Goldstein | |

FOREIGN PATENT DOCUMENTS

EP       0421158       4/1991

OTHER PUBLICATIONS

PCT Priority Document: WO-2006/119986.*
Nezel et al., "Gas selective optical sensors for fire detectors", CHIMIA Int'l J. for Chem., Sep. 2001, pp. 725-731, vol. 55, No. 9, Swiss Chem. Soc.
Liu et al., "Studies on a potentiometric urea biosensor based on an ammonia electrode and urease, immobilized on a Y-aluminum oxide matrix", Analytica Chimica Acta, Apr. 10, 1997, pp. 161-169, vol. 341, Issue 2-3.
Nakagawa et al., "Detection of organic molecules dissolved in water using a y-Al2O3 chemiluminescence-based sensor", Analytical Sciences, Feb. 1998, pp. 209-214, vol. 14, Japan Society for Analytical Chemistry.
Engels et al., "Zur modifizierung hochreaktiver alumini-umoxidubergangsformen" ("Modification of highly reactive transition aluminas") Zeitschrift fur Anorganische und Allgemeine Chemie, Nov. 9, 2004, pp. 381-387, vol. 621, No. 3, Verlag GmbH & Co.
Carraway et al., "Photophysics and photochemistry of oxygen sensors based on luminescent transition-metal complexes", Analytical Chemistry, 1991, pp. 337-342, vol. 63, No. 4.
Lazarin et al., "A platinum electrode coated with a copper (II) aminopropyl complex-cellulose acetate membrane and its use for dissolved oxygen reduction", J. Membrane Sci., Aug. 15, 2003, pp. 175-184, vol. 221, Issue 1-2.
Zhang et al., "Microporous aluminum oxide membrane-based optical interferometric sensor", Mol. Cryst. Liquid Cryst., Nov. 1999, pp. 489-492, vol. 337, No. 1.
International Search Report from PCT/EP2006/004396 by H. Luethe of the European Patent Office, 4 pages, completed Jul. 19, 2006, mailed Sep. 5, 2006.
European Search Report from EP 05010163 by D. Semino of European Patent Office, 3 pages, Sep. 29, 2005, Munich, Germany.
Written Opinion of the International Searching Authority from PCT/EP2006/004396 by H. Luethe of the European Patent Office, 5 pages, Sep. 5, 2006.
International Preliminary Report on Patentability from PCT/EP2006/004396 by Yolaine Cussac of International Bureau of WIPO, 6 pages, Nov. 13, 2007.

\* cited by examiner

*Primary Examiner* — Ling Xu
(74) *Attorney, Agent, or Firm* — Florek & Endres PLLC (57) ABSTRACT

A gas permeable membrane for the optical measurement of the partial pressure and/or the concentration of a gas species, the membrane comprises a porous light-transmissible membrane matrix containing a metal oxide, wherein the membrane matrix is at least partially charged with at least one gas-selective compound whose optical characteristics change upon an interaction with a corresponding gas species.

24 Claims, 7 Drawing Sheets

METAL OXIDE MEMBRANE WITH A GAS-SELECTIVE COMPOUND

CROSS REFERENCE TO RELATED APPLICATIONS

The present application claims priority to International Application No. PCT/EP2006/004396, filed May 10, 2006 and to European Patent Application No. 05010163.3, filed on May 10, 2005.

BACKGROUND OF THE INVENTION

Considerable effort has historically been spent in both broad and specific development of sensor technologies and it is still an area of vital importance and interest to the medical, manufacturing, environmental and defense/security communities.

The most successful sensors for determining gases are electrochemical sensors but their use is limited by the stability of the electrode surface and by instabilities in the gas diffusion barrier, because they usually measure the rate of diffusion of the gas to the cathode or to the anode. They are not welcome for in vivo investigations due to the probability of electroshock. For these reasons, photochemical sensors have been developed to determine gas concentrations. Many of them contain organic dyes or organo-metallic compounds as sensing compounds immobilized to gas permeable supports. Immobilization of the sensing compound onto the matrix of the support is a critical step in the fabrication of photochemical sensors since e.g. organic dyes interact directly with the surface of the matrix of the supports so that the properties of the sensing compound strongly depend on the properties of the supportive matrices.

The reproducibility of the chemical surface composition and the surface reactivity of the surface matrices have been proved to be crucial in sensor applications. This is particularly critical in the case of gas sensors where the surface reactions are the origin of the gas detection mechanism.

In 1990 Lang et al. used metal oxide membranes to develop a catalytic gas sensor (EP-0 421 158 A1). Further, U.S. Pat. No. 5,624,640 discloses a sensor for detecting nitrogen oxide having a semiconducting metal oxide layer ($TiO_2$, $ZrO_2$, $SiO_2$ and/or $Al_2O_3$) with a platinum content ranging from 0.01 to 20 weight percent.

U.S. Pat. No. 5,490,490 discloses a gas sensor used for internal combustion engines where the sensor body consists of a porous high-temperature fluorescent inorganic oxide ceramic to generate an optical fluorescence signal.

U.S. Pat. No. 6,251,342 comprises an optical fiber where at least a part of the surface is coated with a sol-gel processed porous uniform mixture of matrix material (alumina, zirconia, titania or silica) or a mixture of any of them with ceramic fluorescent indicator like Cu-ZSM-5 zeolite incorporated therein.

U.S. Pat. No. 5,979,423 describes a fiber-optic gas composition sensor in which sensor body is made with a porous high-temperature fluorescent inorganic oxide ceramic.

Also, there are some relevant papers which use mesoporous semi-conducting oxides for sensor applications. Liu et al. (Anal. Chim. Acta 341, 161 (1997)) propose a potentiometric biosensor for urea based on the immobilization of urease on a gamma-$Al_2O_3$ substrate. Nakagawa et al. (Anal. Sci. 14, 209 (1998)) developed a chemiluminescence sensor made with $Al_2O_3$ for determining organic molecules in water, Zhang et al. (Mol. Cryst. Liquid Cryst. 337, 489 (1999)) describe microporous aluminum oxide membrane-based optical interferometric sensor for determining stearic acid and Lazarin et al. (J. Membrane Sci. 221, 175 (2003)) use a highly dispersed $Al_2O_3$ in a cellulose acetate membrane modified by attaching an organofunctional group to develop a platinum electrode for determining dissolved oxygen.

Other investigations in the gas sensor fields show that it is possible to use gas-sensitive solvent polymer membranes to which is added at least one gas-selective ionophore as well as a chromoionophore and additives such as plasticizers, counterions etc to develop gas-sensor devices (U.S. Pat. No. 6,704,470 B1, U.S. Pat. No. 5,494,640 and Nezel et al. (Chimia 55, 725 (2001)).

Since the present membrane gas sensors have relative low sensitivity values towards the corresponding gas there is a strong need to provide gas-selective compound charged membranes which show an enhanced sensitivity.

SUMMARY OF THE INVENTION

The aforementioned problem is solved by a gas permeable membrane which comprises a porous light-transmissible membrane matrix containing a metal oxide wherein the membrane matrix is at least partially charged with at least one gas-selective compound whose optical characteristics change upon an interaction with a corresponding gas species, the average pore diameter of the membrane matrix ranges from 1 to 50 nanometers, the total pore volume from 1 to 30 $mL/m^2$, and wherein the metal oxide is pseudo-boehmite with the general formula $Al_2O_3.n*H_2O$, wherein n ranges from 1 to 1.5, or an alumina oligomer.

The inventors have shown that the sensitivity of a gas-selective compound mainly relies on a controlled pore-size, i.e., on the pore diameter and on the pore volume per area of the porous membrane matrix, and on the selected metal oxide. The results further suggest that the higher the amount of mesopores in the membrane matrix is the better is the sensitivity of the gas-selective compound in the matrix. According to IUPAC nomenclature, mesopores are pores with a diameter ranging from 1 to 50 nanometers, wherein the term pores is defined in the context of this invention as cavities, which are interconnected via channels.

In the membrane of the present invention all known gas-selective chemical compounds can be incorporated which induce selectivity, wherein the incorporated compound can be retained in the porous system. Besides, the mesoporous structure of the membrane of the present invention permits the co-retention of more than one compound without aggregation.

Further, the membrane admits chemical processes between chemical compounds to run reversibly providing increased photostability and stability to gamma irradiation due to a shielding effect and due to insulation of chemicals which prevents a reaction cascade to run down. In addition, the insulation of reactive chemicals causes higher stability to the ambient. The controlled capillarity of the membrane matrix of the present invention as well as the excellent accessibility of the gas-selective compound increases the reaction and response time.

Also, the mesoporous membrane permits the co-absorb or co-immobilize a number of specific additional compounds which permit to develop selective gas sensitive phases which react reversibly to the specific gas and allow reversible processes between chemical compounds.

Therefore, the membrane of the present invention provides an increased photostability, a higher dispersion and accessibility and, thus, a quick response time, a lower aggregation probability, a relative high stability to gamma irradiation, an insulation of reactive chemicals and a higher stability to the ambient.

Alumina oligomers are $Al_2O_3$—(AlOOH—) crystallites which contain up to 100 Al-atoms, preferably up to 60 Al-atoms and more preferably up to 30 Al-atoms. The oligomers can be formed in a variety of ways involving hydrolysis of the aluminum cation and are commercially available.

In a preferred embodiment of the invention the average pore diameter ranges from 5 to 30 nanometers.

In another preferred embodiment of the invention the porous translucent membrane matrix has elastic and/or flexible properties.

In another preferred embodiment of the invention the total pore volume is larger than 15 $mL/m^2$. Further, in a preferred embodiment the metal oxide consists of metal oxide nanoparticles. In another embodiment of this invention the metal oxide nanoparticles having an average particle size ranging from 10 to 100 nanometers, preferably from 10 to 60 nanometers, more preferably from 15 to 40 nanometers.

The membrane has a dry thickness ranging from 0.5 to 500 micrometer, preferably from 1 to 100 micrometer, more preferably from 5 to 50 micrometer.

Additionally, the membrane matrix comprises a further metal oxide which is preferably selected from the group consisting of $\delta$-$\gamma$—$Al_2O_3$, $SiO_2$, $ZrO_2$, $TiO_2$ or of a mixture of two or more of the foregoing, since these metal oxides allow to form a well-controlled mesoporous structure. In addition to their characteristic providing nano-sized crystallites or particles these metal oxides show extremely high specific porosity and surface area. Besides, metal oxide materials such as e.g. $SiO_2$, $Al_2O_3$ and $TiO_2$ can be purchased at relatively low costs.

In another embodiment of the invention the metal oxide can be positively or negatively charged.

Of all possible oxides of the elements with atomic numbers between 57 and 71 in the periodic system of elements, aluminum oxide/hydroxide is preferred.

This aluminum oxide/hydroxide may be prepared by similar methods as described for example in: Zeitschrift für anorganische Chemie 621, 381 (1995). In another preparation method aluminum oxide/hydroxide is mixed in aqueous solution at a temperature between 20° C. and 95° C. filtered, washed and dried.

The membrane of the present invention preferably comprises one or more binders to improve the flexibility of the membrane. These binders are preferably water soluble polymers including natural and synthetic polymers. Suitable binders are described in U.S. Pat. No. 6,156,419 (from column 3 line 62 to column 4 line 39) and are herewith included into the present invention as preferred binders.

The membrane matrix of the membrane of the present invention comprises in a preferred embodiment additives such as crosslinking agents, surfactants, reactive compounds, fillers or UV absorbers to modified both the physical and the photochemical properties of the membrane matrix.

The polymeric binders mentioned above are preferably crosslinked via a crosslinking agent to harden the membrane and to make the membrane essentially non water soluble. Suitable crosslinking agent are described in U.S. Pat. No. 6,156,419 (from column 4 line 48 to column 4 line 62) and are herewith included into the present invention as preferred crosslinking agent.

The layers may also contain reactive compounds and are modified by the addition of fillers which are described in the U.S. Pat. No. 6,156,419 from column 4 line 63 to column 5 line 12 and are herewith included into the present invention as preferred fillers.

The light stability of the membrane is improved by adding UV absorbers to the membrane matrix, e.g. absorbers such as described in the U.S. Pat. No. 6,156,419 (from column 6 line 9 to column 6 line 33), which are herewith included into the present invention as preferred UV absorbers.

The mesoporous surface may further contain, in addition to the modified aluminum oxide/hydroxide, water soluble metal salts, as for example, salts of the alkaline earth's or salts of the rare earth metal series.

In another preferred embodiment the membrane is arranged on a support, preferably deposited on the support. The support can be a transparent film, a paper, a glass or a silica crystal, a metallic support or a waveguide, preferably a waveguide consisting of a plastic material.

The transparent films can be made from cellulose esters, polyesters, polyamides, polycarbonates, polyimides, polyolefins, poly(vinyl acetals), polyethers, PVC and polysulfonamides. Poly(ethylene terephthalate) are preferred because of their excellent dimensional stability characteristics, their transparent characteristics to visible wavelengths and their stability when they are subjected to gamma irradiation sterilization process.

Preferred supports for the manufacture of optical sensors are glass, silica or plastic fiber optics. Fiber optics are preferred for optical gas sensors for biotechnology applications which can be sterilized by gamma-irradiation. It is further preferred to use glass or silica fiber optics like waveguides and to coat the aluminum oxide/hydroxide on a transparent plastic support.

According to another preferred embodiment the adhesion of the membrane on the support can be enhanced by means of a subbing layer. For example, if a plastic support material is used, e. g. polyester, an additional subbing layer is advantageously coated on the support to improve the bonding of the membrane to the support. Useful subbing compositions are described in U.S. Pat. No. 6,156,419 (from column 5 line 38 to column 5 line 44) and are herewith included into the present invention as preferred subbing compositions.

The gas-selective compound is selected from the group comprising metal complexes, ionophores, chromophores, chromoionophores and any kind of neutral, uncharged or charged, acid and basic dyes, wherein according to another embodiment of the present invention the gas-selective compound is adsorbed and/or immobilized to the surface of the membrane matrix, preferably to the inner surface of membrane matrix.

Also, the nanostructure described in this invention enables the deposition and/or immobilization of more than one selective compound and due to the proximity of these dyes into the mesopores. Thereby, any kind of electron or energy transfer pairs for optical detection and any kind of reference compound/dye can be deposited onto the nanostructure.

The membrane permits the deposition of different gas-selective compounds into their pores. Thereby, it is possible to deposit metallo-organic complexes such as phtallocyanines, cobyrinates, ruthenium(II) bipyridyl and phenanthroline complexes ($ETH^T$ 3003), iridium complexes such as tetrabutylammonium-cis-di(cyano)-N,N-bis(2-phenylpyridine)iridium(III) (N-833), (tetrabutylammonium-cis-di(thiocyanato)-N,N-bis(2-phenylpyridine) iridium(III) (N-837) and N,N-bis(2-phenylpyridine)-(4,4'-dimethylamino-2,2'-bipyridine)iridium(III)) chloride (N-926), manganese, iron and cobalt complexes, inorganic and mixed metal complexes such as the iridium complexes above, ionophores such as ETH 157, ETH 1001, ETH 129 etc, chromoionophores such as nileblue and meldola blue and its derivatives, e.g. ETH 5350, ETH 5294, ETH 2439, as well as azobenzol and its derivatives such as ETH 5315 and trifluoroacetophenone and its derivatives (ETH$^{TT}$ 4001, ETH$^{TT}$ 4012), trifluoroacetostilbene and its derivatives (ETH$^{TT}$ 4004, ETH$^{TT}$ 4014), aminoperylene and its derivatives (N-Aminoperylene-3,4:9,10-tetracarboxylbisimide). In addition any kind of neutral, acid and basic dyes, pH- and metal-indicators can be added, adsorbed and co-adsorbed to the mesoporous structure. Examples are: benzoxazine dyes and its derivatives, azo dyes and its derivatives such as 4-aminoazobenzol, fluorescin and fluorescein and its derivatives, cyanine dyes, ketocyanine dyes, calmagite, 9-phenyl-2,3,7-trihydroxy-6-fluoron, celestine blue, hydroxynaphtol blue, naphtol blue black, phenol red, acid green, Janus green, brilliant yellow, nitrazine yellow, various phtaleins and phtalein esters such as naphtolphtalein etc.

The membrane is provided with a hydrophobic or hydrophilic barrier layer, a semipermeable reflecting layer and/or a refractive index adjustment layer for luminescent enhancement. A multilayer structure can combine more than one nanostructured layer one on top of the other or, in addition, an array of nanostructured layers.

A membrane according to the invention is preferably sterilizable in an autoclave and/or with gamma irradiation.

The membrane is preferably a gas-selective sensing membrane for the optical measurement of the partial pressure and/or the concentration of a gas species. Absorbance, reflectance, luminescence (fluorescence, phosphorescence and chemiluminescence) emission intensity or lifetime, polarization, refractive index, infrared absorbance or any optical signal which can be correlated with the concentration or partial pressure of the gas are suitable to do the optical evaluation of the nanostructure invented.

Further, in another preferred embodiment the membrane is a gas-selective sensing membrane for the optical measurement of the partial pressure and/or the concentration of CO, wherein the metal oxide is a positively or negatively charged metal oxide, e.g. AlOOH, $SiO_2$, $ZrO_2$ etc, the average pore diameter of the membrane matrix ranges from 5 to 50 nanometers and the total pore volume from 1 to 30 mL/m$^2$.

In another embodiment the membrane is a gas-selective sensing membrane for the optical measurement of the partial pressure and/or the concentration of $NO_2$, wherein the metal oxide is a positively charged metal, e.g. AlOOH(+) and $SiO_2$ (+), whereas the average pore diameter of the membrane matrix ranges from 5 to 50 nanometers and the total pore volume from 1 to 30 mL/m$^2$.

Additionally, the membrane is a gas-selective sensing membrane for the optical measurement of the partial pressure and/or the concentration of $O_2$, wherein the metal oxide is a positively or negatively charged metal oxide, e.g. AlOOH, $SiO_2$, $ZrO_2$ etc, the average pore diameter of the membrane matrix ranges from 5-50 nanometers preferably larger than 15 nm, and the total pore volume ranges from 1-30 mL/m$^2$ and is preferably larger than 15 mL/m$^2$.

In a further preferred embodiment of the invention the membrane matrix comprises a further metal oxide which is $SiO_2$.

Further, it is preferred that the gas-selective compound is Fe-phtalocyaninato-di-decylamine (FePc(DA)$_2$) or Fe-phtalocyaninato-di-benzylamine (FePc(BA)$_2$).

In another preferred embodiment of the membrane according to the invention, the membrane matrix further comprises an amine compound. Amine compounds are able to stabilize the gas-selective compound so that the long-term stability of the membrane is increased by means of amines incorporated in the membrane matrix. Preferred amines are mono- or diamines, especially those amines which bind to FePc under normal conditions.

In another aspect, the invention relates to the use of the membrane for the measurement of the presence, the partial pressure and/or the concentration of a gas in cultivation flask and bags, incubators, medical devices, in gas atmospheres, solutions, vapors and exhaust gases, as well as the use of the membrane in sensor arrays, in mobile fiber optical sensors and in remote sensing devices. The gas-selective sensor membrane described in this invention may be used to analyze gas concentrations and partial pressures of dissolved gases, vapors, exhaust gases, biogases etc. for environmental and food technology, biotechnological and medical applications, for cultivation control in bioreactors, in life sciences, in production control etc. The gas selective nanostructured sensors can be implemented in cultivation flasks or bags, sensor array devices, mobile fiber optical sensors and any kind of remote sensing device. They are sterilizable by gamma-irradiation and heat.

For the use in solutions it can be necessary to provide the membrane with a protection layer, which is preferably formed from a polypropylene containing polymer preferably a mono oriented polypropylene, a teflon layer etc.

Preferred gas-selective sensors are those applied to measure, monitor and detect the following gases: oxygen and ozone, nitrogen dioxide ($NO_2$) and nitrogen oxide (NO), ammonia ($NH_3$), hydrogen diamine ($NH_2$—OH) and other nitrogen oxides, sulfur dioxide ($SO_2$) and hydrogen sulfide (HS), volatile uncharged sulfur compounds, hydrogen cyanide (HCN), hydrogen halides (HCl, HF, HBr, HJ), carbon monoxide (CO), carbon dioxide ($CO_2$), volatile organic compounds (VOCs), volatile solvents, alcohol, ketones, aldehydes, amines.

Gas-selective sensors can be applied to reversible continuous monitoring of the gas partial pressure and concentration in air or in any other medium. The sensor can be used as disposable sensor for on site detection or as exposure probe especially if the chemical reaction within the nanostructured membrane is not reversible.

Further, the invention provides a method for the manufacture of the membrane, comprising the steps of:
a) preparing a dispersion of the metal oxide in a first solvent;
b) applying a layer of said dispersion onto a support;
c) drying the applied layer;
d) dissolving a gas-selective compound whose optical characteristics change upon an interaction with a corresponding gas species, in a second solvent;
e) applying the solution of step d) onto the metal oxide layer of step c);
f) drying the charged membrane of step e).

According to a preferred embodiment the method is carried out in an automated process. Preferably, steps a) to c) are carried out in an automated process.

This mesoporous membrane permits the deposition of different gas-selective compounds into their pores. For example, the membrane can be dipped in a solution of the chemical compounds, a drop of the solution can be put on the membrane and the solvent is evaporated or the membrane can be placed on a spin-coating device and the solution can be transferred onto the rotating metal oxide membrane with a syringe.

The coating solution or coating dispersions according to step a) can be coated onto a support by any number of suitable procedures. Usual coating methods include extrusion coating, air knife coating, doctor blade coating, cascade coating or curtain coating. The coating solutions may also be applied using spray techniques. The mesoporous membrane layers can be built up from several single layers that can be coated one after the other or simultaneously.

According to a preferred embodiment a surfactant is added to the dispersion obtained in step a) to improve the smoothness and evenness of the layer. The mesoporous sensory layers according to this invention are in general coated from aqueous solutions or dispersions containing all necessary compounds. In many cases, it may be necessary to add surfactants to those coating solutions or dispersions allowing for smooth coating and evenness of the layers.

Further, the second solvent is preferably selected from the group consisting of water, ethanol, methanol, dioxane, acetone, acetonitrile, chloroform, thf, aniline, pyridine, ionic liquids or mixtures of two or more of the foregoing. Different solvents may be used for solving the gas-selective compounds such as water, ethanol, methanol, dioxane, cyclohexanone, acetone, acetonitrile, chloroform, thf, dmso, dmf, toluene, aniline, pyridine, ionic liquids or mixtures of them.

Additionally, additives such as glycerin, glycine, glycol and its derivatives as well as with plasticizers such as o-NPOE, o-CPOE, DOS, TBP, etc., acids and bases, and surfactants such as Tween, antioxidants such as ascorbic acid etc. can be added to the second solvent.

DETAILED DESCRIPTION OF THE INVENTION

The present invention relates to a mesoporous membrane with a gas-selective compound showing new and advantageous features in the development of gas sensors.

Figure 1:
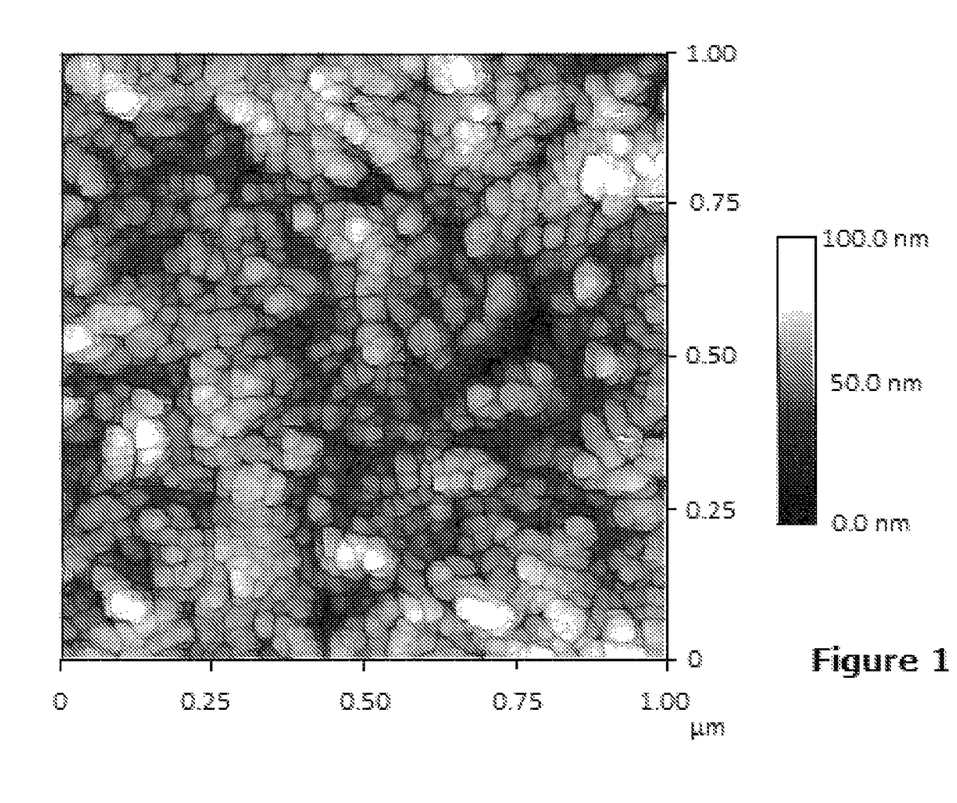
FIG. 1: Atomic force microscopy (AFM) image of the AP200/19 AlOOH mesoporous matrix. Scan size 1.000 μm, scan rate 1.969 Hz, number of samples 512, Image data Height and data scale 100.00 nm.

FIG. 1 shows an atomic force microscopy (AFM) image of a membrane (AP 200/19 A100H mesoporous matrix) according to a first embodiment of the invention. The membrane is formed as a gas-sensor membrane comprising a solid-support, a nanostructured membrane consisting of a metal oxide layer with a controlled and reproducible porosity wherein the membrane contains mesopores (the pore diameter ranges from 1 to 50 nanometers), macropores (the pore diameter is greater than 50 nanometers) and micropores (the pore diameter is less than 1 nanometer). The chemical gas-selective compounds which induce selectivity and are responsible for the spectral change upon interaction with the specific gas are adsorbed to the surface of the pores along with additives.

The co-retention of different compounds within the mesoscopic pores distributed on the molecular level is responsible for the high rate of interaction. The molecular interactions studied were preferably reversible processes. The molecular dispersion and the insulation of co-reactive compounds within the mesopores induce increased photostability, higher capillarity and accessibility of chemicals, lower aggregation probability, higher stability to gamma irradiation and higher stability to ambient.

EXAMPLES

Test Procedures

The following test procedures were used to evaluate and compare the mesoporous membrane described here with state-of-the art technology for developing gas sensors.

Evaluation of luminescent gas-selective sensors: evaluation of the quantum yields. The equation used for determining the quantum yield is:

$$\phi_{L,X} \cdot K_{opt} = \phi_{L,r} \cdot \frac{(D/A_{exc})_X}{(D/A_{exc})_{r,Liquid\ membrane}}$$

where the subscripts X denote the substance whose quantum yield id determined and r the reference substance (2.25·10$^{-6}$ M Rhodamine 101 in ethanol); $K_{opt}$ is the optical factor which steams from the considerably higher refractive index of the membrane compared to the liquid membrane; D is the integrated area under the emission spectra; $A_{exc}$ is the absorbance at the exciting wavelength. The $\phi_{L,r}$ (the luminescence quantum yield of Rhodamine 101) is assumed to be 1.0.

Stern-Volmer Constant

For determining the Stern-Volmer constants for the dyes supported on Aluminum oxide/hydroxide membranes is necessary to consider a multiple-site model. In this situation, the overall Stern-Volmer expression is the superposition of Stern-Volmer expressions resulting in a summation over all sites:

$$\frac{I_0}{I} = \left[\sum_{i=1}^{m} \frac{f_i}{1+K_{sv,i} \cdot pO_2}\right]^{-1}$$

where m is the number of microdomains, $f_i$ denotes the fractional contribution to the $i^{th}$ microdomains, $K_{sv,i}$ is the Stern-Volmer constant associated with the $i^{th}$ component and $pO_2$ is the partial pressure of oxygen in the medium.

Where m=2 the experimental data can be fitted using a two-site model proposed by Demas and co-workers and called Demas' model (Anal. Chem. 63, 337 (1991)).

$$\frac{I_0}{I} = \left[\frac{f_1}{1+K_{sv,1} \cdot pO_2} + \frac{f_2}{1+K_{sv,2} \cdot pO_2}\right]^{-1}$$

In this expression, $f_i$ denotes the fractional contribution of the total luminescence emission from the luminophore located at site type i under unquenched conditions that exhibits a discrete Stern-Volmer quenching constant given by $K_{sv,i}$. In its simplest embodiment, such a representation is mathematically equivalent to a biexponential decay of I(t) where each component independently fulfils a classic Stern-Volmer relationship.

Example 1

Aluminum Oxide/Hydroxide for Developing Oxygen Sensors a) Preparation of Aluminum Oxide/Hydroxide 50 g of the aluminum oxide/hydroxide DISPERAL 100/2 (available from SASOL GmbH, Hamburg, Germany) of formula $AlOOH.nH_2O$ (77.2% $Al_2O_3$) were dispersed for 15 minutes un vigorous mechanical stirring at a temperature of 20° C. in 948 g of doubly distilled water. Afterwards temperature was increased to 90° C. and stirring was continued for 15 minutes at this temperature. The solid was filtered, washed three times with doubly distilled water and dried to 110° C.

b) Preparation of a Coating Solution 8 g of the solid from example 1 a) were added to a mixtures of 63 g of doubly distilled water and 0.96 g of concentrated acetic acid (80%). The resulting dispersion was exposed for 3 minutes at 40° C. to ultrasound. Afterwards, 8 g of a solution of polyvinyl alcohol (10% by weight, hydrolysis degree 98-99%, Molecular weight 85,000 to 146,000) (available from ALDRICH Chemie, Buchs, Switzerland) were added and the resulting coating solution was again exposed to ultrasound for 3 minutes.

c) Coating 100 g/m² of this coating solution were coated at a temperature of 40° C. onto a transparent polyester support. The coated support was then dried 60 minutes at a temperature of 30° C.

d) Preparation of Gas-Selective Sensors, Deposition of the Gas-Selective Compounds:

4 different dyes were tested for developing oxygen sensors. A Ruthenium complex called $ETH^T$-3003 and three Iridium complexes called N-926, N-833 and N-837. 3 mg of ETH-3003, 3 mg of N-926, 6 mg of N-833 and 6 mg of N-837 were weighted and solved in 2 mL of chloroform separately. A mesoporous membrane was placed in a spin-coating device with a chloroform-saturated atmosphere. 0.1 mL of solution was transferred onto the rotating membrane with a syringe. The resulting gas-selective mesoporous membrane was placed in ambient air for drying.

The preparation of the gas-selective membranes by adding a gas selective compound solution to the membrane was surprisingly simple to carry out. It is assumed that the gas selective compound adsorbs to the surface of the mesopores after the evaporation of the solvent. In addition, the evaporation of the solvent was surprisingly fast because it is usually necessary to heat up the membranes to eliminate completely the solvent as a result of the high porosity and strong capillary forces of the mesoporous membrane. For example, THF, chloroform and other non-polar organic solvents evaporate in less than 10 seconds, ethanol, methanol and other polar organic solvents take less than 30 seconds, and even water takes less than 50 seconds.

e) Evaluation for Oxygen Sensors

Table 1 shows the quantum yields of these dyes immobilized within the invented mesoporous membrane relative to Rhodamine 101 (general reference dye). The luminescent dyes mentioned above immobilized within the aluminum oxide/hydroxide film show similar quantum yields as in polymer films, so the immobilization in this new support does not change their quantum yield. However, surprisingly, we found that the mixed iridium complexes N-926, N-833 and N-827 show generally much higher quantum yield (85% for N-926) compared to the ruthenium(II)-complexes such as $ETH^T$ 3003 which show generally less than 40% quantum yield.

Table 1. In addition to the quantum yield, the Stern-Volmer constants $K_{sv}$ for the oxygen-sensitive dyes in a polystyrene (PS) and in an AlOOH membrane according to Demas' model are shown.

TABLE 1

| Dye | Aluminum oxide/hydroxide membrane | | PS membrane | |
|---|---|---|---|---|
| | Quantum yields | $K_{sv,1}$ | Quantum yields | $K_{sv}$ |
| ETH-3003 | 0.34 ± 0.03 | 71.1 ± 10.5 | 0.19 ± 0.05 | 1.6 ± 0.0 |
| N-926 | 0.85 ± 0.05 | 101.9 ± 11.6 | 0.80 ± 0.05 | 1.2 ± 0.0 |
| N-833 | 0.14 ± 0.03 | 34.9 ± 10.1 | 0.60 ± 0.05 | 0.3 ± 0.0 |
| N-837 | 0.43 ± 0.04 | 87.1 ± 21.9 | 0.38 ± 0.05 | 0.7 ± 0.0 |

The table shows that Stern-Volmer constant $K_{sv}$ increases at least forty times when immobilizing the metal complexes in the invented nanostructure as compared to implementation within polymer membranes. So, their immobilization in the membrane according to the invention increases considerably their applicability for developing oxygen sensors.

Example 2

Aluminum Oxide/Hydroxide for Developing $CO_2$ Sensors

Using the same membrane as described in Example 1 a) to c) other $CO_2$ sensible mixture was tested (in place of Ruthenium and Iridium complexes).

a) Deposition of the Gas Sensory Compounds $10^{-4}$ to $10^{-3}$ mmol of dye (α-Naphtholphthalein) and $10^{-4}$ to $10^{-3}$ mmol (200 μL) of tetraoctylammonium hydroxyl were dissolved in 400 μL of methanol. 0.2 to 0.5 mL of the solution was transferred onto the mesoporous membrane with a micropipette. The resulting gas-selective membrane was placed in ambient air for drying.

Surprisingly, the sequence in which the compounds are added to the membrane is relevant. Opposite to other media, the spin coating technique cannot be used to transfer the gas-selective compounds onto the rotating membrane. The two compounds which have to be incorporated into the membrane have to be dropped onto the membrane in separate solutions. When both α-Napththolphthalein and tetraoctylammonium hydroxide are solved in the same solution and dropped onto the membrane together, the resulting optode does not respond to $CO_2$. Further, the dye α-Napththolphthalein has to be dropped first to the membrane and, when the solvent (methanol) is evaporated, the second compound (tetraoctylammonium hydroxide) can be added to the mesoporous membrane.

b) Evaluation of the $CO_2$ Sensor

To evaluate the applicability of our invention for the development of $CO_2$-sensors, the selective gas membrane described in Example 2 a) was fixed into a flow-cell and exposed to different partial pressures of $CO_2$ in synthetic air while the absorbance at 655 nm was measured.

Figure 2:
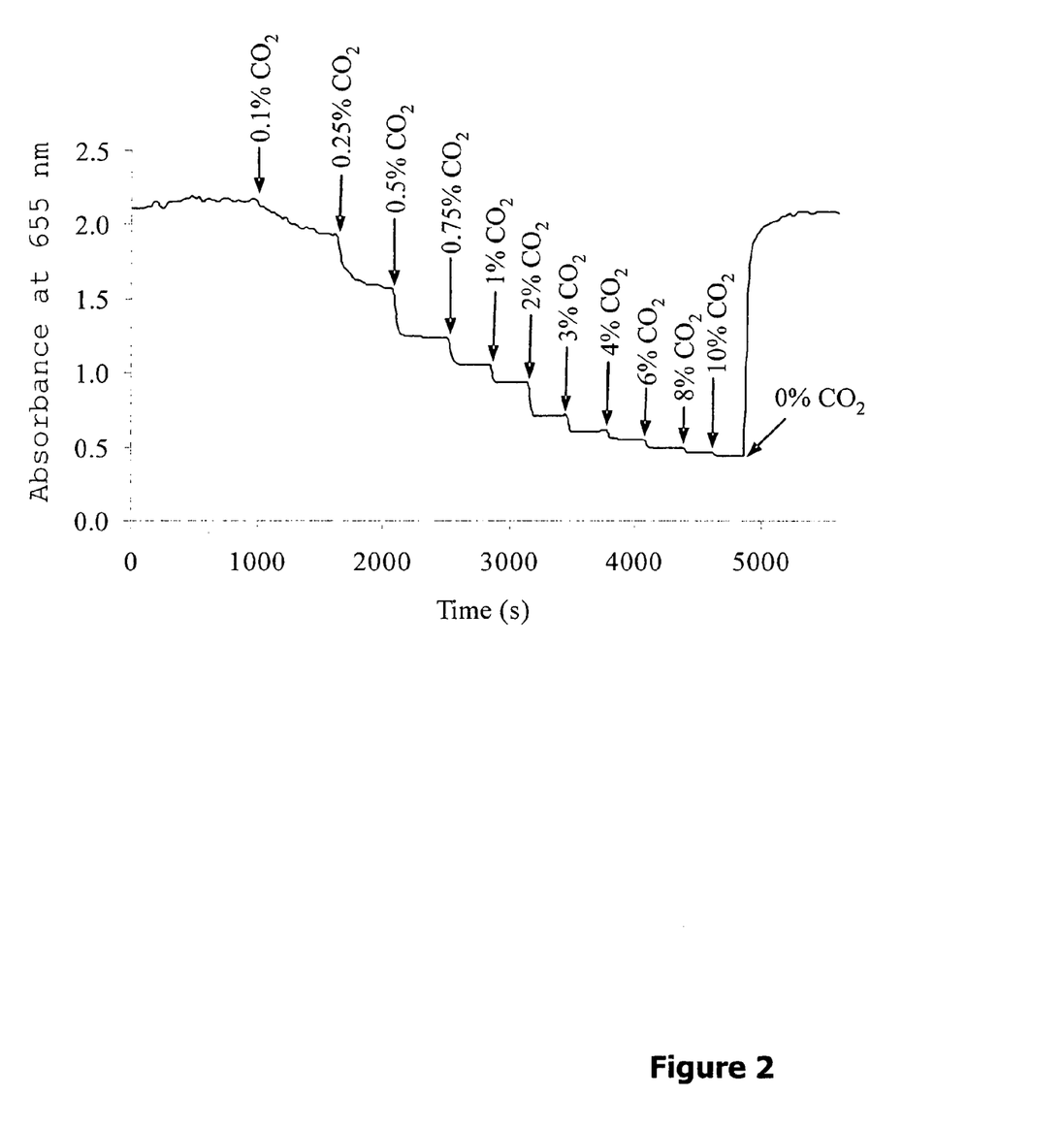
FIG. 2: Response of the $CO_2$-selective film to 0.1 up to 10% v/v carbon dioxide. Optical evaluation of the absorbance change at $\lambda$=655 nm (y-axis); response time in seconds on the x-axis (1000 s=16.67 min).

FIG. 2 shows the experimental results. It is shown that the $CO_2$-selective membrane responds to different percentages of $CO_2$ with varying absorbance intensity measured in transmission mode at a wavelength of 655 nm. In addition the correlation between the absorbance and the percentage of $CO_2$ can be calculated. Therefore the nanostructured membrane fulfills the conditions for developing $CO_2$-sensors which are sensitive to 0.1 to 5 vol/vol % $CO_2$.

Example 3

Aluminum Oxide/Hydroxide for Developing $NO_x$ Sensors

Using the same membrane as described in Example 1 a) to c), a membrane cocktail as used for $NO_2$-selective sensors (Tomas Nezel (2002) Ph. D. thesis Nr. 14602, Swiss Federal Inst. of Technology (ETH Zürich, Switzerland)) was tested.

a) Deposition of the Gas Sensory Compounds 0.1 to 1.0 mg of dye (Iron-Phthalocyanine) was dissolved in 0.6 mL of THF using an additive to solubilize the dye. A mesoporous membrane was placed in a spin-coating device in THF-saturated atmosphere. 0.1 to 0.4 mL of solution was transferred onto the rotating membrane with a syringe. The resulting gas-selective mesoporous membrane was placed in ambient air for drying.

b) Evaluation for $NO_2$ Sensors

To evaluate the applicability of our invention to the development of a $NO_2$-sensor, the selective gas membrane described in Example 3 a) was fixed into a flow-cell and exposed to different concentrations of $NO_2$ in synthetic air while the absorbance was measured at 659 nm.

Figure 3:
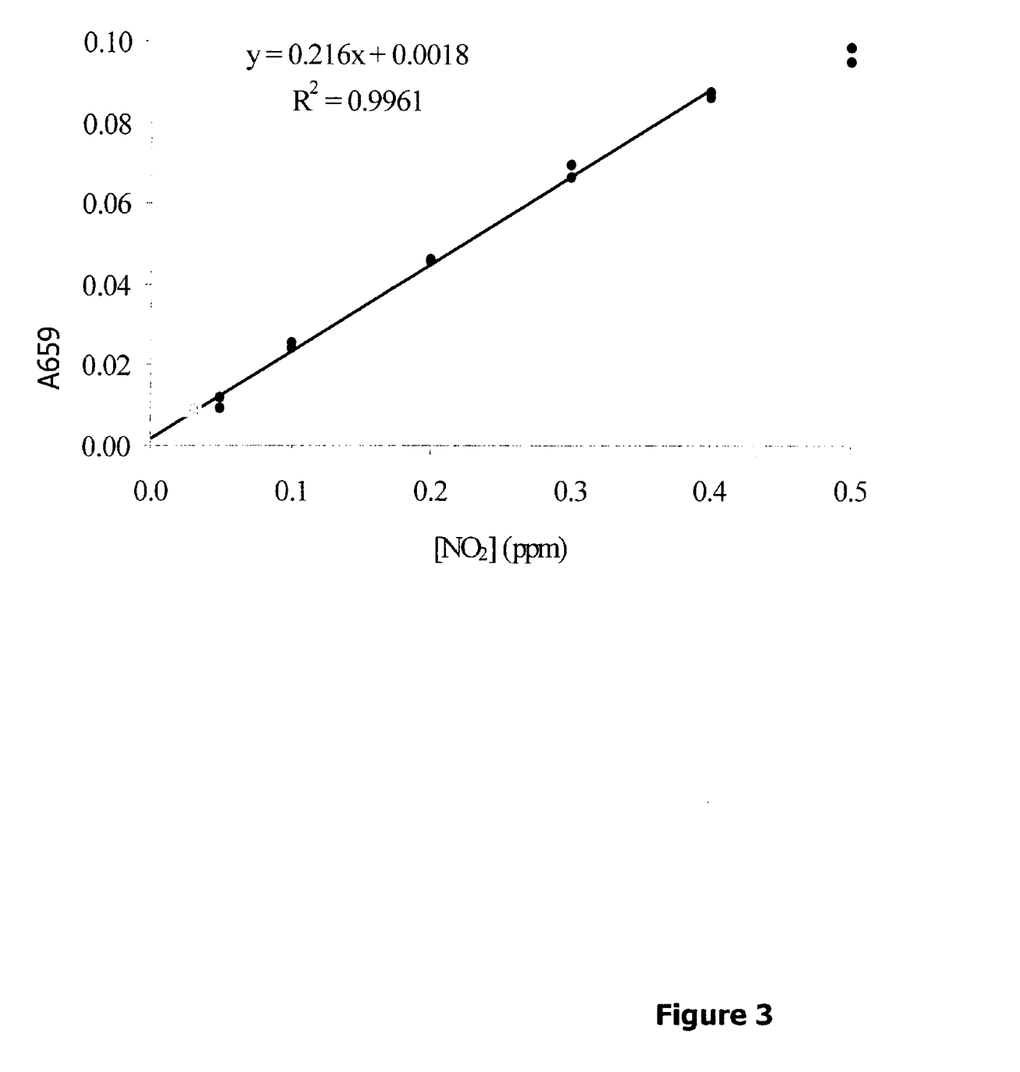
FIG. 3: Response of the $NO_2$-selective film to 0 up to 400 ppb nitrogen dioxide. Optical evaluation of the absorbance change at $\lambda$=659 nm (y-axis); concentration of nitrogen dioxyde.

FIG. 3 shows the experimental results. The sketch shows that the $NO_2$-selective membrane responds to different concentrations of $NO_2$ with a change in absorbance.

Example 4

Oxygen-Selective Membranes Based on Energy Transfer of Luminescence Between Two Metal Complexes Co-Immobilized to Aluminum Oxide/Hydroxide The same nanostructured membrane described in Example 1 a) to c) was used as matrix to incorporate the chemically active and selective compounds.

a) Deposition of the Gas Sensory Compounds

Three different cocktails were prepared by dissolving 1 to 10 mg of $ETH^T$-3003 with 1 to 10 mg of N-926, N-833 and N-837, respectively, in 2 mL of chloroform. Then, the mesoporous membrane was placed in a spin-coating device in a chloroform-saturated atmosphere. Then, 0.1 mL of the cocktail was transferred onto the rotating nanostructure membrane with a syringe. The resulting gas-selective mesoporous membrane was placed in ambient air for drying.

In this case, the donor and acceptor compounds can be solved in the same solution and the membrane can be loaded with the resulting solution. In addition, both compounds can be incorporated separately obtaining the same results as when using the avove mentioned single solution. Therefore, the co-immobilization of more than one compound is surprisingly simple to perform when the compounds show similar chemical structures.

b) Evaluation of the $O_2$ Sensing Capabilities

To demonstrate the energy transfer between the Iridium complexes as a donor at 530 nm emission and the ruthenium (II) complex as an acceptor, the Stern-Volmer plots were obtained using the excitation wavelengths of the Iridium dyes and measurement the fluorescence emission at the emission wavelength of the Ruthenium(II) complex. Table 2 shows the Stern-Volmer constants for these gas-selective mesoporous membrane using the Demas' model.

TABLE 2

| Donor | Acceptor | $K_{sv,1}$ | Wavelength (nm) | |
|---|---|---|---|---|
| | | | Excitation | Emission |
| N-926 | ETH-3003 | 61.4 ± 13.2 | 400 | 620 |
| N-833 | ETH-3003 | 47.8 ± 5.5 | 402 | 620 |
| N-837 | ETH-3003 | 74.4 ± 1.8 | 398 | 620 |

Table 2 shows that the Stern-Volmer constant determined at an emission wavelength of 620 nm by varying the oxygen partial pressure in air are very similar to those obtained for Iridium complexes incorporated into the mesoporous membrane at 530 nm. This demonstrates that more than one compound can be adsorbed to the mesopores, and that energy transfer between donor and acceptor compounds is surprisingly practically complete due to the proximity of the complexes what is exceptional for this nanostructured material.

Using this nanostructured energy transfer membrane, it is possible to profit from the high Stern-Volmer constants of the Iridium complexes at 530 nm and simultaneously to profit from the emission at wavelengths>620 nm of the Ru(II)-complexes (beyond the absorbance of hemoglobin and the emission of biological compounds) which renders the invention most attractive for biological and biotechnological applications.

Example 5

Photostability of Dyes Supported in Aluminum Oxide/Hydroxide Membranes

The same nanostructured AlOOH-membranes as described in Example 1 were used. To demonstrate the photostability of the membranes according to the invention, the membranes used in example 1 were illuminated with a mercury lamp during 16 hours in presence and in absence of oxygen (air and nitrogen atmosphere, respectively). The distance between the lamp and the membrane was 25 cm, so the lamp illuminates the membranes with an intensity of 1.0 $kW/m^2$.

Table 3 shows the quantum yield ($\Phi$) before and after the irradiation, indicating also the percentage of decreasing in their quantum yields when they are subdued to 16 hours under a mercury lamp in nitrogen and air atmospheres.

TABLE 3

| | Dye | $\Phi_{before}$ | $\Phi_{after}$ | % decreasing$\phi$ |
|---|---|---|---|---|
| In $N_2$ | ETH-3003 | 0.34 ± 0.03 | 0.20 ± 0.06 | 41.0 |
| | N-926 | 0.85 ± 0.05 | 0.47 ± 0.12 | 44.8 |

TABLE 3-continued

|  | Dye | $\phi_{before}$ | $\phi_{after}$ | % decreasing$\phi$ |
|---|---|---|---|---|
|  | N-833 | 0.14 ± 0.03 | 0.12 ± 0.04 | 19.3 |
|  | N-837 | 0.43 ± 0.04 | 0.17 ± 0.02 | 59.4 |
| In air | ETH-3003 | 0.34 ± 0.03 | 0.16 ± 0.06 | 53.8 |
|  | N-926 | 0.85 ± 0.05 | 0.43 ± 0.11 | 49.7 |
|  | N-833 | 0.14 ± 0.03 | 0.11 ± 0.04 | 27.1 |
|  | N-837 | 0.43 ± 0.04 | 0.16 ± 0.03 | 62.2 |

Illuminating with a powerful lamp during 16 h in presence and absence of oxygen has shown that the membrane according to the invention provides a photostable environment and it can be used for a long period of time with a LED. The intensity of the used lamp was 1.0 Kw/m² while the intensity of a 450 nm LED is 0.19 Kw/m².

The experimental results also show that the results of photobleaching are practically the same in $N_2$ atmospheres and in air.

Example 6

Sterilization of Aluminum Oxide/Hydroxide Membranes by Gamma Irradiation

The same nanostructured membranes as described in Example 1 were used. In this case, the membranes were exposed to gamma-irradiation and autoclave sterilization processes and the Stern-Volmer constants before and after theses processes were calculated and compared. Table 4 shows the Stern-Volmer constants for these gas-selective mesoporous membranes using the Demas' model.

TABLE 4

| Dye | | $f_1$ | $K_{sv,1}$ | $f_2$ | $K_{sv,2}$ |
|---|---|---|---|---|---|
| ETH-3003 | Before | 0.93 ± 0.03 | 71.1 ± 10.5 | 0.11 ± 0.04 | 1.8 ± 1.2 |
|  | After autoclave | 0.52 ± 0.05 | 20.1 ± 12.2 | 0.48 ± 0.06 | 0.4 ± 0.0 |
|  | After Gamma-ray | 0.86 ± 0.06 | 55.6 ± 3.6 | 0.10 ± 0.03 | 0.7 ± 0.7 |
| N-926 | Before | 0.87 ± 0.02 | 101.9 ± 11.6 | 0.16 ± 0.02 | 1.4 ± 0.6 |
|  | After autoclave | 0.67 ± 0.03 | 88.8 ± 9.7 | 0.33 ± 0.05 | 0.4 ± 0.0 |
|  | After Gamma-ray | 0.74 ± 0.09 | 87.5 ± 12.6 | 0.26 ± 0.09 | 0.4 ± 0.1 |
| N-833 | Before | 0.55 ± 0.07 | 34.9 ± 10.1 | 0.45 ± 0.07 | 0.4 ± 0.0 |
|  | After autoclave | — | — | — | — |
|  | After Gamma-ray | 0.46 ± 0.01 | 37.1 ± 1.8 | 0.54 ± 0.01 | 0.1 ± 0.0 |
| N-837 | Before | 0.74 ± 0.15 | 87.1 ± 21.9 | 0.27 ± 0.15 | 0.7 ± 0.1 |
|  | After autoclave | 0.37 ± 0.08 | 54.2 ± 10.5 | 0.63 ± 0.05 | 0.3 ± 0.0 |
|  | After Gamma-ray | 0.62 ± 0.02 | 101.9 ± 7.6 | 0.38 ± 0.02 | 0.3 ± 0.0 |

Table 4 shows that the Stern-Volmer constant obtained before and after the gamma-irradiation sterilization process are very similar. Also, the Stern-Volmer constants were re-obtained nine month later and the values were exactly the same, so it is possible to sterilize these gas-selective membranes and to conserve the sensor device without any change in the sensor's properties. Therefore, this sensor is appropriate to applications in biological fluids and in the field of biotechnology.

These surprising results were never reported before and depend presumably on the use of a metal oxide as membrane matrix material instead of an organic compound as in the prior art.

Example 7

The specific pore volume can be calculated from the total pore volume and the coating weight. Table 5 shows structure parameters of different membranes deposited on a support.

TABLE 5

| Foil | Oxide | Charge | Pore volume (ml/g) | Coating weight (g/m²) | Total pore volume (mL/m²) | Pore diameter (nm) | PVA (%) |
|---|---|---|---|---|---|---|---|
| AP171/14 | AlOOH | + | 0.6 | 28.5 | 17.1 | 14.2 | 9 |
| AP200/19 | AlOOH | + | 0.7 | 28.5 | 20.0 | 19.2 | 10 |
| AP148/6 | AlOOH | + | 0.52 | 28.5 | 14.82 | 6.3 | — |
| AP74/11 | AlOOH | + | 0.26 | 28.5 | 7.41 | 11.3 | — |
| ZP13/16 | $ZrO_2$ | + | 0.19 | 6.84 | 1.3 | 16 | 5 |
| SP88/31 | $SiO_2$ | + | 1.1 | 8.0 | 8.8 | 31 | 25 |
| SN27/32 | $SiO_2$ | − | 1.35 | 2 | 2.7 | 31.8 | 8 |
| SN54/32 | $SiO_2$ | − | 1.35 | 4 | 5.4 | 31.8 | 6 |

Example 8

The experiments show that there are two different microdomains within the metal oxide membranes which show different sensitivity to luminescence quenching by oxygen. Referred to the experiment with oxygen-selective optodes, the variation of the fluorescence signal can be explained with a two-site model (Demas' model). The equation is:

$$\frac{I_0}{I} = \left[\frac{f_1}{1 + K_{SV,1} \cdot pO_2} + \frac{f_2}{1 + K_{SV,2} \cdot pO_2}\right]^{-1}$$

where $f_i$ denotes the fractional contribution of the total luminescence emission from the luminophore located at site type i under unquenched conditions that exhibits a discrete Stern-Volmer quenching constant given by $K_{SV,i}$. Table 6 shows the oxygen sensing properties of dyes immobilized onto AlOOH and PS (polystyrene) membranes.

TABLE 6

| Dye | AlOOH matrix | | | | PS matrix |
|---|---|---|---|---|---|
| | $f_1$ | $K_{sv,1}$ | $F_2$ | $K_{sv,2}$ | $K_{sv}$ |
| EHT$^T$-3003 | 0.93 ± 0.03 | 71.1 ± 10.5 | 0.11 ± 0.04 | 1.8 ± 1.2 | 1.6 ± 0.0 |
| N-926 | 0.87 ± 0.02 | 101.9 ± 11.6 | 0.16 ± 0.02 | 1.4 ± 0.6 | 1.2 ± 0.0 |
| N-833 | 0.55 ± 0.07 | 34.9 ± 10.1 | 0.45 ± 0.07 | 0.4 ± 0.0 | 0.3 ± 0.0 |
| N-837 | 0.74 ± 0.15 | 87.1 ± 21.9 | 0.27 ± 0.15 | 0.7 ± 0.1 | 0.7 ± 0.0 |

Figure 5:
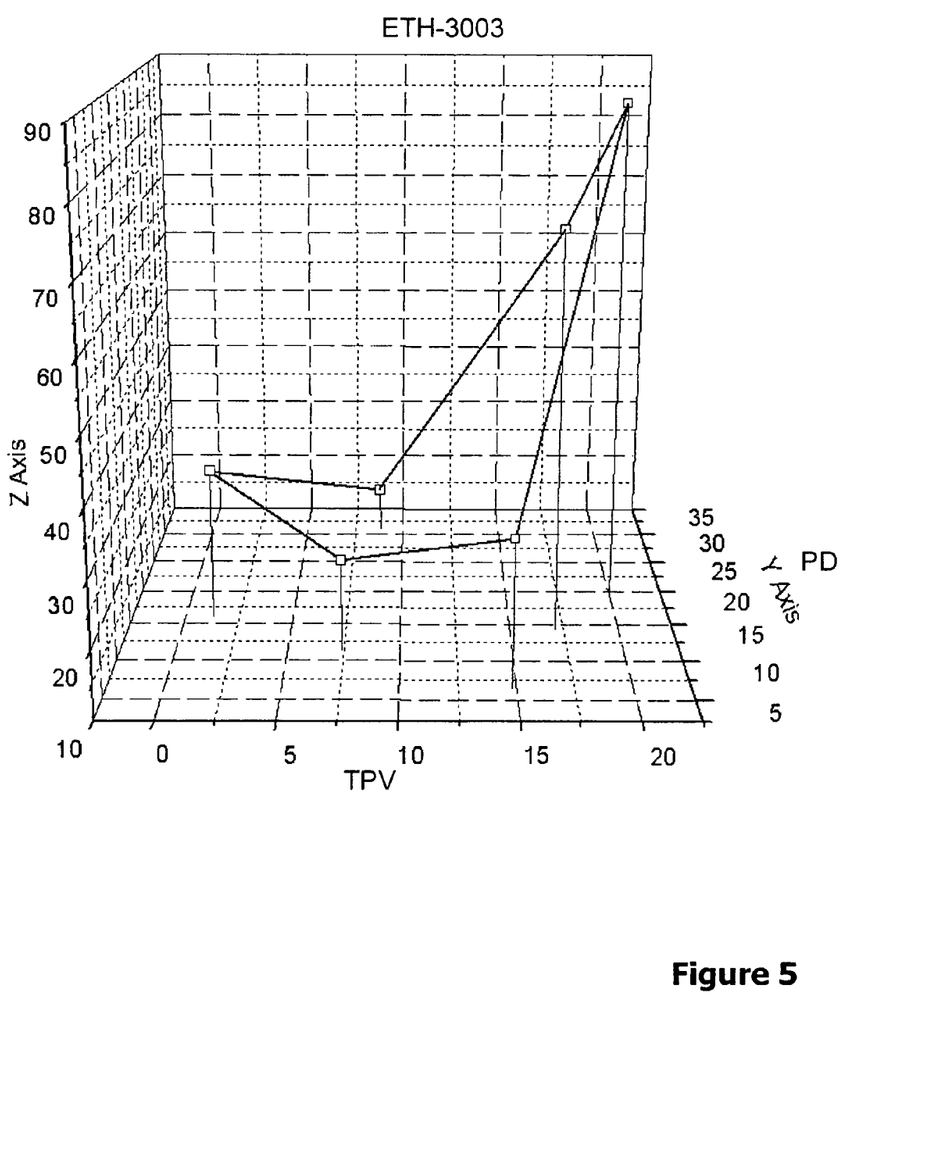
FIG. 5: Effect of the porosity on the Stern-Volmer constant. PD/10$^{-9}$ m, pore diameter; $K_{sv,1}$, Stern-Volmer constant; TPV/mL m$^{-2}$, total pore volume. The positively charged metal oxides are aluminum, silicon and zirconium oxide. Stern-Volmer constant investigated using ETHT 3003.
Figure 6:
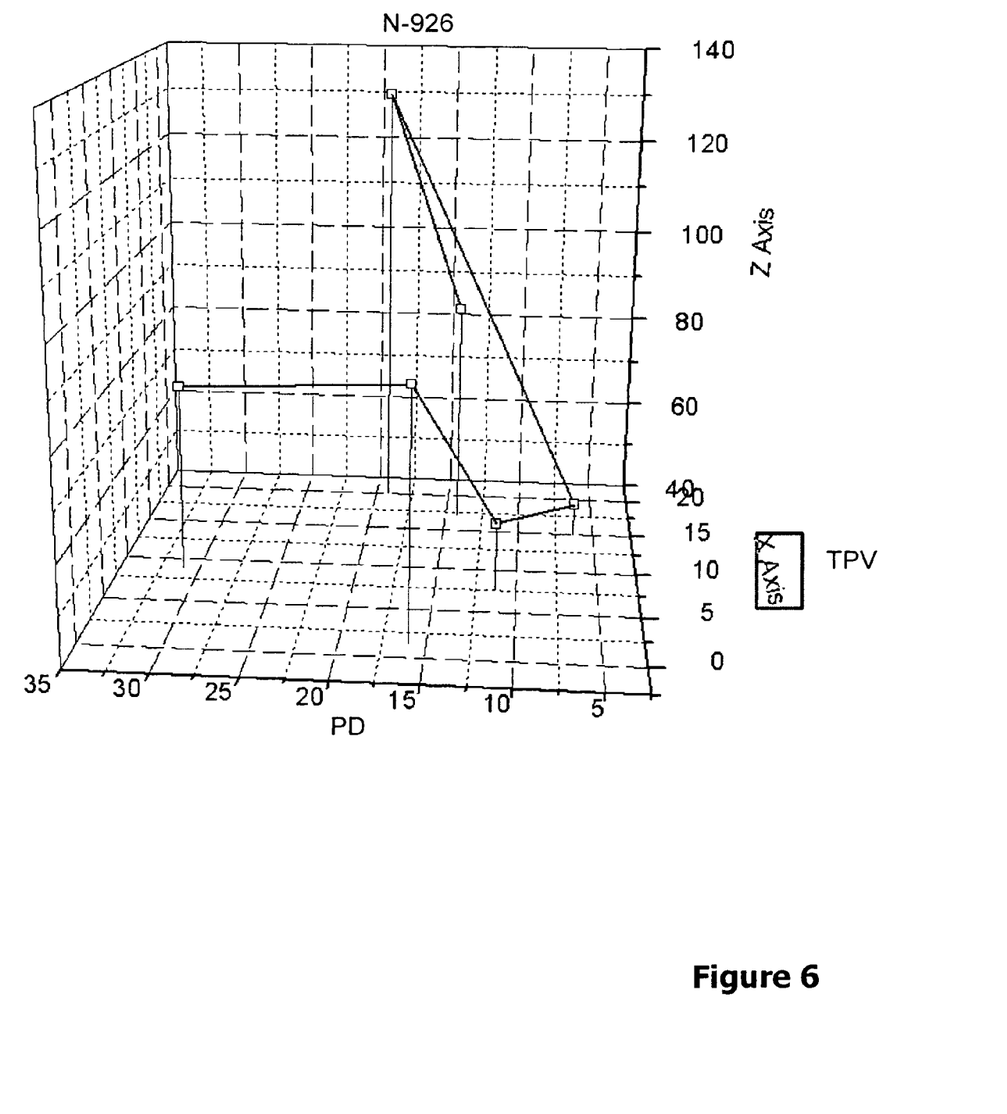
FIG. 6: Effect of the porosity on the Stern-Volmer constant. PD/10$^{-9}$ m, pore diameter; $K_{sv,1}$, Stern-Volmer constant; TPV/mL m$^{-2}$, total pore volume. The positively charged metal oxides are aluminum, silicon and zirconium oxide. Stern-Volmer constant investigated using N-837 as metal complexes.

The results listed in table 6 are averaged values which have been calculated from at least three measurements which have been performed under the same conditions. The results can be interpreted as follows:
- two different $K_{sv}$ values ($K_{sv1}$ and $K_{sv2}$) can be determined as a result of metal complexes with a different reactivity;
- the higher value of $K_{sv1}$, which is equivalent to a higher sensitivity has an amount of the total luminescence quenching of the complex ranging from 55% to 93%;
- the lower value of $K_{sv2}$ which is indicative for a lower sensitivity has an amount of the total luminescence quenching of the complex ranging from 11% to 45%. The $K_{sv2}$ value is approximately identical with the results determined for polystyrene membranes. This strongly suggests that the constant $K_{sv2}$ and therefore the lower sensitivity corresponds to metal complexes deposited in macropores;
- comparative measurements of six positive charged metal oxide membranes have been performed and lead to the conclusion that the constant $K_{sv1}$ which is for optical measurements the more attractive magnitude depends on the pore diameter and the total pore volume (FIGS. 5 and 6).

Further, the inventors found that the AlOOH membrane is not heterogeneous. The dye is found in two different environments which show different accessibility to oxygen. In conclusion, the metal oxide membranes offer two different sites to host the dyes, one with a very high $K_{sv}$ and with high fractional population (mesopores) and other not very much populated and with $K_{sv}$ similar to that measured for the PS-membrane (macropores). Because capillarity forces occur inside the mesopores the fractional population inside them is very high and also the oxygen is driven into these pores. Only few molecules of the dye and low level of oxygen can be in touch with the macropores. Also, it is possible to observe the advantages to use mesopores versus macropores, $K_{SV,1}$ is the Stern-Volmer constant of the dye into mesopores, $K_{SV,2}$ is for macropores and $K_{SV-PS}$ is the Stern-Volmer of the same dye coated with polystyrene. The experimental results show that:

$$K_{SV,1} >>>> K_{SV,2} \approx K_{SV-PS}$$

Example 9

Figure 4:
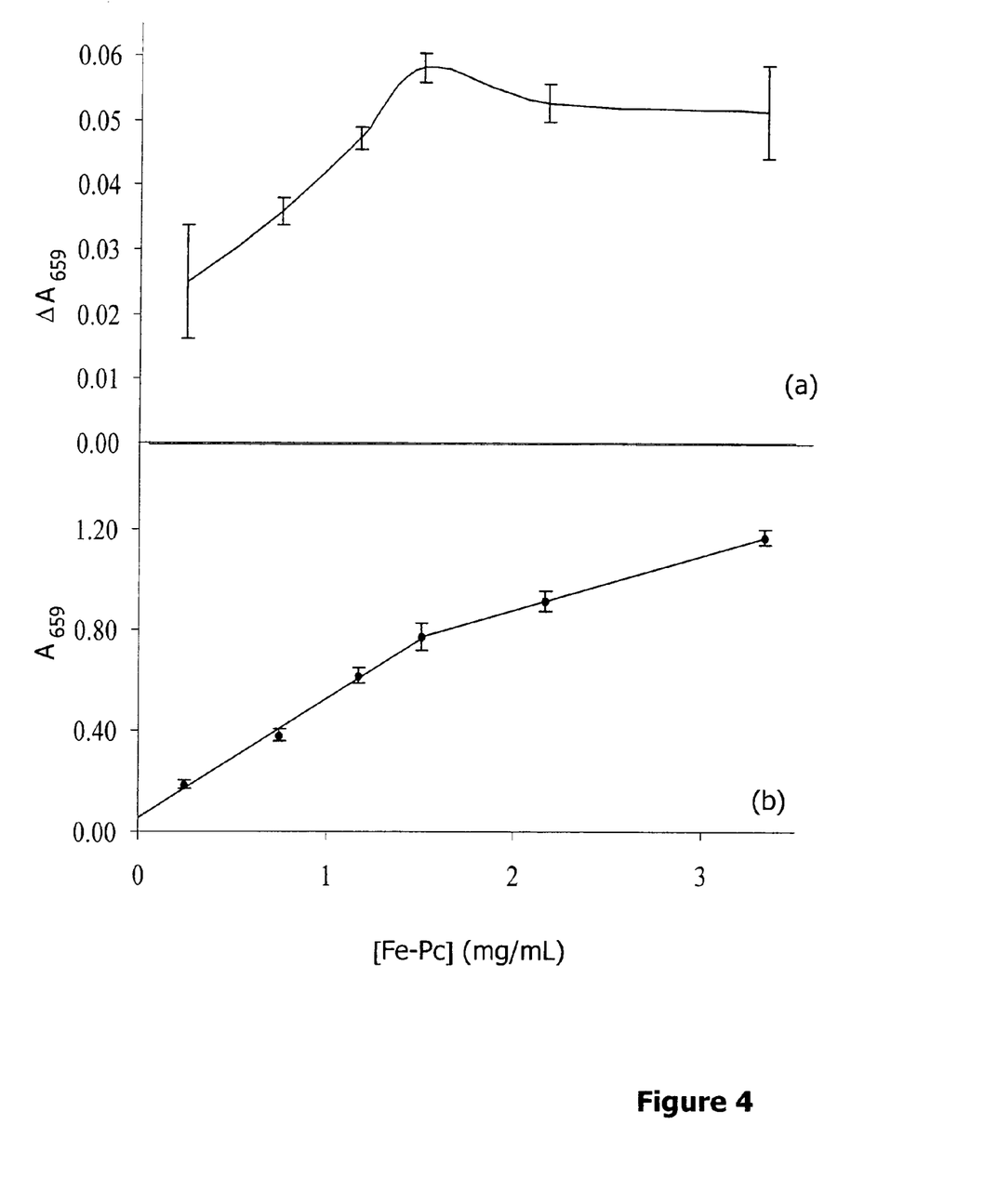
FIG. 4: Effect of the $Fe^{II}Pc$ concentration on the a) sensor response ($A_0$-$A_x$; $A_0$, absorbance before $NO_2$ exposure; $A_x$, Absorbance on exposure to 200 ppb $NO_2$) and b) the absorbance of the optode in absence of $NO_2$. [DA]=12.5 mg mL$^{-1}$, AP200/19 AlOOH membrane, $\lambda_{max}$=659 nm, relative humidity 50% and flow-rate 200 mL min$^{-1}$.

By means of gas sensors selective for $NO_2$ the inventors have shown that the lining of the different pores with a gas-selective compound takes place step-by-step. Further, it has been shown that the lining of the different pores depends on the volume of the membrane solution with which the gas-selective compound is applied to the membrane (FIG. 4).

The variation of the $A_{659}$ and the $\Delta A_{659}$ can be explained by the presence of two different environments. FIG. 4a shows that an increase in the Fe-Pc concentration provides an increase in the $\Delta A_{659}$ up to 1.5 mg mL$^{-1}$ and higher Fe-Pc concentrations produce a plateau. Nevertheless, the $A_{659}$ of the optode increases with concentration higher that 1.5 mg mL$^{-1}$ (see FIG. 4b). So, an increase in the absorbance does not provide an increase in the $\Delta A_{659}$. This phenomena is due to in the metal oxide membranes where two different kind of pores (mesopores and macropores) can be traced. Fe-Pc begins to fill up the mesopores due to capillary forces ([Fe-Pc]<1.5 mg mL$^{-1}$) and when the mesopores are full ([Fe-Pc]= 1.5 mg mL$^{-1}$), the macropores start to fill up. For this reason, FIG. 4b shows two different slopes before and after 1.5 mg mL$^{-1}$, indicating different molar absorption coefficients demonstrating that two different environments exist. When $NO_2$ is in contact with the optode, the gas diffuses into the mesopores very quickly due to capillary forces, so the Fe-Pc concentration within the macropores does not affect the $\Delta A_{659}$ but increases the absorbance of the optode.

Example 10

Thermostability Study

One of the most important requirements for $NO_2$ or CO-sensing membranes is stability at elevated temperatures. For example, for medical applications they should be stable at body temperature (~38° C.), for environmental control they may be stable at least at 60° C., and for fire alarm sensors a long-term stability at temperatures of 60° C. are required. To check the thermostability of the $NO_2$ and CO-sensing membranes, different membranes incorporating FePc(DA)$_2$ and FePc(BA)$_2$ were prepared following a general procedure (see example 1) and stored at various temperatures (4, 25, 60 and 80° C.). These membranes were evaluated subsequently with 200 ppb $NO_2$ or 50 ppm CO at 50% humidity.

From these experiments (data not shown) it was concluded that the sensing membranes containing FePc(DA)$_2$ are stable for at least one month at 4° C. and at 25° C. When they were stored at 60° C., they are loosing 45% of their sensitivity during the first 24 h and more than 86% after 2 days. If they are stored at 80° C. they are loosing 55% after 1 day and more than 95% after the second day. The FePc(BA)$_2$ sensing films were even less stable, they lost 60% at 60° C. and more than 80% after the first day.

The low thermostability of the membranes was assigned to two different phenomena: on the one hand, oxidation processes which may oxidize the amine and, on the other hand, leaching (i.e. evaporation) of the N-donor ligand which is exchanged by NO$_2$ or CO. The generally observed decrease in absorbance of the sensing layers and the intensive odour of the membranes when they were removed from the oven indicate that an evaporation process is going on. The higher thermostability of the film based on FePc(DA)$_2$ as compared to those based on FePc(BA)$_2$ can be explained by the higher boiling point of 1-aminodecane.

To clarify which process, oxidation of the complex and amine or evaporation of the N-donor ligand, is responsible for the low thermostability of the membranes, NMR studies on FePc(DA)$_2$ and FePc(BA)$_2$ were performed at several temperatures between 289 and 348 K in the absence of oxygen under nitrogen atmosphere.

In order to probe the effect that oxygen may cause, the complexes FePc(DA)$_2$ and FePc(BA)$_2$ were subjected to the same NMR studies at the same temperature programme in presence of air. No change in the spectra compared to the set obtained in inert atmosphere was obtained. These results give evidence that oxidation processes are less important. At least these processes are much slower and require more time in order to modify the composition of the membranes.

In other words, it is the evaporation of the N-donor ligand that is responsible for the less thermostability of the membranes. To increase the stability, it was decided to make use of compounds added to the nanostructured membrane matrix which prevent the evaporation of the amine but still allow diffusion of CO and NO$_2$.

Example 11

Chemical Modification of Novel Metal Oxide Membranes in Order to Increase the Thermostability of FePc(DA)$_2$ In order to increase the thermostability, an appropriate chemical modification of the nanoparticulate membrane matrix was proposed. By embedding an amine into the metal oxide matrix directly (for example 1-amino-n-decane or 1,10-diamino-n-decane) the evaporation of the amine solvent was supposed to be prevented (so called monoamine and diamine modified nanostructured matrices, M and D). Anti gas fading agents, G, were added in order to avoid the degradation of active compounds by oxidation, and embedding alumina oligomers, A, $A^L$, $A^{30}$, should improve the diffusion of CO and NO$_2$.

Table 7 shows the nomenclature and composition of chemically-modified positively-charged membranes (here also referred to as supports) according to the invention used in thermostabilty studies. Abbreviations for the additives: M, monoamine; D, diamine; A, alumina oligomers; G, anti gas-fading additives. Further abbreviations: SP, SiO$_2$ positively charged; AP, AlOOH positively charged; Diam., Diamine modified; Monoam., monoamine modified; g.f., anti gas fading; Al-Ol, alumina oligomers.

TABLE 7

| Foil | Pore volume (mL/g) | Coating weight (g/m$^2$) | Total pore volume (mL/m$^2$) | Pore diameter (nm) | Modified by |
| --- | --- | --- | --- | --- | --- |
| SP237/27D | 1.41 | 19 | 26.8 | 27 | Diam. |
| SP268/27D | 1.41 | 19 | 26.8 | 27 | Diam. |
| SP168/27D | 1.41 | 11.9 | 16.8 | 27 | Diam. |
| SP268/27DG | 1.41 | 19 | 26.8 | 27 | Diam. + g.f. |
| SP268/27DA | 1.41 | 19 | 26.8 | 27 | Diam. + Al—Ol |
| SP16827DA | 1.41 | 11.9 | 16.8 | 27 | Diam. + Al—Ol |
| SP268/27DAG | 1.41 | 19 | 26.8 | 27 | Diam. + Al—Ol + g.f. |
| SP168/27MA | 1.41 | 12 | 16.8 | 27 | Monoam. + Al—Ol |
| SP168/27A$^L$ | 1.41 | 12 | 16.8 | 27 | Locron Al—Ol |
| SP168/27A$^{30}$ | 1.41 | 12 | 16.8 | 27 | Al$_{30}$$^{18+}$ Al—Ol |
| AP268/16 | 0.64 | 42 | 26.8 | 16.5 | — |
| AP168/16 | 0.64 | 26.3 | 16.8 | 16.5 | — |
| AP268/16G | 0.64 | 42 | 26.8 | 16.5 | g.f. |

The supports called AP168/16 and AP268/16 are non-chemically modified nanostructured solid supports.

Figure 7:
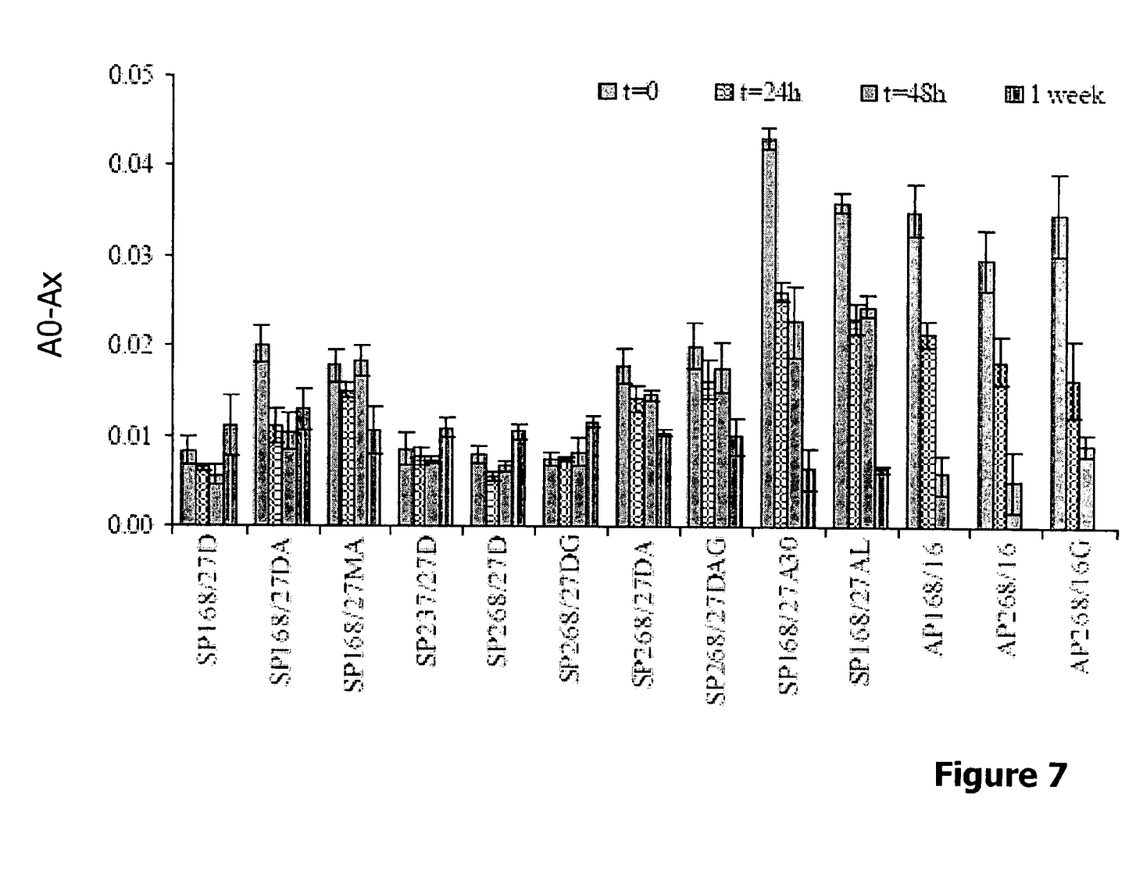
FIG. 7: Thermostability study of sensing membranes incorporating FePc(DA)2 within chemically modified solid supports at 60° C. $A_0$ is the absorbance before exposure to $NO_2$, and $A_x$ is the absorbance on exposure to 200 ppb $NO_2$ for 300 s in air at 50% RH.

FIG. 7 shows the variation in the sensitivity ($A_0$-$A_x$) of the membranes during one week at 60° C.; where $A_x$ is the absorbance on exposure to 200 ppb NO$_2$ for 300 s at 50% RH and at a flow-rate of 200 mL min$^{-1}$; $A_0$ is the absorbance in synthetic air (50% RH and at a flow-rate of 200 mL min$^{-1}$).

Generally, the non-chemically modified supports AP168/16 and AP268/16 and the only alumina modified SP168/27A$^L$ and SP168/27A$^{30}$ show the best sensitivity at t=0 indicating that the sensitivity of the solid surface is due to the chemistry of the boehmite AlOOH or the alumina oligomers. The addition of an anti gas-fading agent doesn't additionally drop the sensitivity, $A_0$-$A_x$, (AP268/16 and AP268/16G, SP268/27D and SP268/27DG, and SP268/27DA and SP268/27DAG show similar $A_0$-$A_x$). If mono- or diamines are added, the sensitivity is significantly decreased (see $A_0$-$A_x$ of SP168/27D, SP237/27D and SP268/27D); however alumina oligomers are able to compensate this effect partially (compare the amine-modified membranes SP168/27MA, SP168/27DA with SP168/27D, and SP268/27DA with SP268/27D), but provide lower sensitivity than the non-chemically modified membranes.

At an elevated temperature of 60° C. (t>0), the membranes which contain a anti gas-fading agent show the same thermostability as those without anti gas-fading agent, i.e. AP168/

16, AP268/16 and AP268/16G; the incorporation of an amine improves the thermostability: the D membranes (SP168/27D, SP237/27D, SP268/27D) are stable for at least 1 week at 60° C. but the sensitivity of these membranes is low. The addition of alumina oligomers provides membranes which show an analytical performance between non-chemically modified and amine modified membranes.

In summary, the addition of an anti gas-fading agent does neither affect the sensitivity nor the thermostability. Therefore, oxygen, ozone or other gases are supposed not to be responsible for the degradation of the membranes at higher temperatures, which is in agreement with the NMR results where no oxidation process was detected.

The incorporation of amines into the membrane matrix improves the stability of the membrane but decreases the sensitivity. Since the sensitivity of the metal complex to CO and $NO_2$ relies on the reversible exchange of one and only one amine ligand at the metal center, it was supposed that this mechanism is competed by the amine added to the matrix. The iron(II) complex may be chemically bound to the matrix and therefore the evaporation of the N-donor ligand is reduced but also the ligand exchange is reduced which results in lower sensitivity to the gas molecules. Since only one free amine is coordinating to the metal center, the exchange with $NO_2$ or CO is less efficient. Similar effects are observed when the $FePc(DA)_2$ was incorporated into negatively charged $SiO_2$-matrices.

In summary the addition of structurally bound amine to the matrix reduces the sensitivity of the membranes to CO and $NO_2$, but influences the thermostability in a positive manner. The incorporation of both, alumina oligomers and amines or boehmit-AlOOH and amines provides sensing membranes which are more stable than the non-chemically modified membranes and more sensitive than the amine-modified membranes. The two chemical agents show to have an additional effect; on the one hand the structural amine provides higher thermostability, and on the other hand the alumina oligomers or the boehmit-AlOOH improves the sensitivity.

The invention claimed is:

1. A gas permeable membrane for the optical measurement of the partial pressure and/or the concentration of a gas species, the membrane comprising a porous light-transmissible membrane matrix comprising a metal oxide wherein the membrane mix is at least partially charged with at least one gas-selective compound by incorporation, whose optical characteristics changes upon an interaction with a correspondingly selected gas species, characterized in that the average pore diameter of the membrane matrix ranges from 1 to 50 nanometers and the total pore volume ranges from 1 to 30 mL/m$^2$, and in that the metal oxide is taken from the group consisting of pseudo-boehmite with the general formula $Al_2O_3$n*$H_2O$, wherein n ranges from 1 to 1.5, and an alumina oligomer.

2. The membrane according to claim 1, characterized in that the average pore diameter ranges from 5 to 30 nanometers.

3. The membrane according to claim 1, characterized in that the total pore volume ranges from 15 mL/m$^2$ to 30 mL/m$^2$.

4. The membrane according to claim 1, characterized in that the metal oxide consists of metal oxide nanoparticles.

5. The membrane according to claim 4, characterized in that the metal oxide nanoparticles have an average particle size ranging from 10 to 100 nanometers.

6. The membrane according to claim 1, characterized in that the membrane has a dry thickness ranging from 0.5 to 500 micrometers.

7. The membrane according to claim 1, characterized in that the membrane matrix further comprises a further metal oxide which is selected from the group consisting of δ-γ—$Al_2O_3$, $SiO_2$, $ZrO_2$, $TiO_2$ and mixtures thereof.

8. The membrane according to claim 1, characterized in that the membrane matrix further comprises one or more binders.

9. The membrane according to claim 1, characterized in that the membrane matrix further comprises one or more additives taken from the group consisting of crosslinking agents, surfactants, reactive compounds, fillers and UV absorbers.

10. The membrane according to claim 1, characterized in that the membrane is deposited on the support.

11. The membrane according to claim 10, characterized in that the support is formed for one or more materials taken from the group consisting of a transparent film, a paper, a glass crystal, a silica crystal, a metallic support, a waveguide, a waveguide consisting of a plastic material, and combinations thereof.

12. The membrane according to claim 10, characterized in that the adhesion of the membrane on the support is enhanced by means of a subbing layer.

13. The membrane according to claim 1, characterized in that the gas-selective compound is selected from the group consisting of metal complexes, ionophores, chromophores, chromoionophores, neutral acid dyes, neutral basic dyes, uncharged acid dyes, uncharged basic dyes, charged acid dyes, charged basis dyes and combinations thereof.

14. The membrane according to claim 1, characterized in that the gas-selective compound is adsorbed and/or immobilized to the surface or the inner surface of the membrane matrix.

15. The membrane according to claim 1, characterized in that the membrane is provided with a hydrophobic barrier layer, a semipermeable reflecting layer and/or a refractive index adjustment layer.

16. The membrane according to claim 1, characterized in that the membrane matrix further comprises a second metal oxide comprising $SiO_2$.

17. The membrane according to claim 1, characterized in that the gas-selective compound is taken from the group consisting of Fe-phtalocyaninato-di-decylamine ($FePc(DA)_2$) and Fe-phtalocyaninato-di-benzylamine ($FePc(BA)_2$).

18. The membrane according to claim 1, characterized in that the membrane matrix further comprises an amine compound.

19. A method for measuring the presence, the partial pressure and/or the concentration of a gas in one or more of a cultivation flask and bag, incubator, medical device, gas atmosphere, solution, vapour and exhaust gas, wherein said method comprises using a membrane according to claim 1.

20. A sensor, taken from the group consisting of sensor arrays, mobile fiber optical sensors and remote sensing devices, comprising the membrane according to claim 1.

21. A method for manufacture of a membrane according to claim 1, comprising the steps of:
   a) preparing a dispersion of the metal oxide in a first solvent;
   b) applying a layer of said dispersion onto a support;
   c) drying the applied said layer;
   d) dissolving a gas-selective compound whose optical characteristics change upon an interaction with a correspondingly selected gas species, in a second solvent;
   e) applying the solution of step d) onto the metal oxide layer of step c); and
   f) drying the charged membrane of step e).

22. The method according to claim 21, characterized in that a surfactant is added to the dispersion of step a).

23. The method according to claim 21, characterized in that the second solvent is selected from the group consisting of water, ethanol, methanol, dioxane, acetone, acetonitrile, chloroform, tetrahydrofuran (thf), aniline, pyridine, ionic liquids and mixtures thereof.

24. The method according to claim 21, characterized in that the second solvent is provided with one or more additives taken from the group consisting of glycerine, glycine, glycol, plasticizers, surfactants and mixtures thereof.

* * * * *